US011051729B1

(12) United States Patent
Yamamura

(10) Patent No.: US 11,051,729 B1
(45) Date of Patent: Jul. 6, 2021

(54) OXYGEN SATURATION MEASURING DEVICE, PROBE ADAPTED TO BE USED THEREFOR, AND OXYGEN SATURATION MEASURING METHOD

(71) Applicant: CAPMET, INC., Wilmington, CA (US)

(72) Inventor: Haruo Yamamura, Tokyo (JP)

(73) Assignee: CAPMET, INC., Wilmington, CA (US)

( * ) Notice: Subject to any disclaimer, the term of this patent is extended or adjusted under 35 U.S.C. 154(b) by 0 days.

(21) Appl. No.: 16/746,208

(22) Filed: Jan. 17, 2020

(51) Int. Cl.
*A61B 5/1455* (2006.01)
*A61B 5/00* (2006.01)

(52) U.S. Cl.
CPC ........ *A61B 5/14552* (2013.01); *A61B 5/6843* (2013.01); *A61B 2560/0233* (2013.01)

(58) Field of Classification Search
None
See application file for complete search history.

(56) References Cited

U.S. PATENT DOCUMENTS 8,588,878 B2 * 11/2013 Li ...................... A61B 5/14551
600/323
2011/0029247 A1 * 2/2011 Kalathil ............... A61B 5/1455
702/19

FOREIGN PATENT DOCUMENTS

JP      2006075354      3/2006
JP      2019048050      3/2019

* cited by examiner

*Primary Examiner* — Eric F Winakur
*Assistant Examiner* — Marjan Fardanesh
(74) *Attorney, Agent, or Firm* — C. Brandon Browning; Brian Sattizahn; Maynard, Cooper & Gale, PC

(57) ABSTRACT

An oxygen saturation measuring apparatus capable of measuring arterial blood oxidation saturation (SpO2), and tissue oxygen saturation (rSO2), safely, easily and economically at a desired position of a biological body for a long time continuously. A ROM stores the distance information between a light emitting unit and a light receiving unit situated corresponding to the depth of a target intended to be measured for tissue oxygen saturation, a light emission driving unit makes the light emitting unit emit light in an amount of light corresponding to the distance information, MPU makes the light emitting unit emit a pulses capable of measuring the tissue oxygen saturation, MPU applies pulse capable of measuring the tissue oxygen saturation from the light emission driving unit to the light emitting unit, and the pulse increasing unit increases the amount of pulses from MPU for a predetermined time to pulses capable of measuring the arterial blood oxygen saturation.

17 Claims, 6 Drawing Sheets

OXYGEN SATURATION MEASURING DEVICE, PROBE ADAPTED TO BE USED THEREFOR, AND OXYGEN SATURATION MEASURING METHOD

BACKGROUND OF THE INVENTION

Field of the Invention

The present invention relates to an oxygen saturation measuring apparatus, a probe adapted to be used therefor, and an oxygen saturation measuring method and, more in particular, it relates to an oxygen saturation measuring apparatus, a probe adapted to be used therefor and an oxygen saturation measuring method for measuring near infrared light emitted from a light emitting unit to a biological body and received by a light receiving unit.

Description of the Related Art

A pulse oximeter has been known as medical equipment capable of measuring arterial oxygen saturation (hereinafter referred to "SpO2") and pulse rate by attaching a detector called as a probe (for example, refer to Japanese Patent Laid-Open No. 2019-48050).

Oxygen is supplied to a human body by means of blood circulating in the body. Oxygen taken from a lung by respiration is transported to a whole body being combined with hemoglobin contained in the blood. The pulse oximeter is adapted to measure the ratio of hemoglobin bonded with oxygen among the hemoglobin contained in the blood flowing through the arterial blood transported from the heart to the whole body.

The probe of the pulse oximeter comprises a light emitting unit that emits light, i.e., two types of near infrared lights at different wavelengths and a light receiving unit that detects the light emitted from the light emitting unit on the side opposite to the light emitting unit. The two types of lights emitted from the light emitting unit transmit through finger tips, earlobes, etc. and the light receiving unit measures the transmitted lights on the opposite side.

Since the light absorption amount to the hemoglobin contained in the blood is different between the two types of lights depending on the state of bonding with oxygen, SpO2 can be measured by measuring the light transmitting through or reflected from the finger tips, the earlobes, etc. by the light receiving unit, and further analyzing the difference of the absorption amount between the two types of lights.

The light applied to the biological body, for example, the finger tips, the earlobes, etc. transmit through tissue layers other than blood, arterial layers, venous layers and reaches a light receiving unit that detects light while undergoing light absorption in each of the layers. Further, arterial blood pumped out from the heart and transported to the whole body by pulsation moves through the vessels in a waveform referred to as a pulse wave due to the change in the blood pressure or volume in peripheral vessel systems.

Only the pulsating arterial blood changes the thickness by the pulse wave within an extremely short time, and the thickness is unchanged in the tissue layer other than the blood and the venous layer. Since the amount of transmission light also changes along with the change of the thickness, the light detected by the light receiving unit also changes. Thus, the light fluctuation component detected by the light receiving unit is a thickness changing portion, that is, information for the arterial blood.

The changing component of the arterial blood can be measured by a removing unchanged portion from the pulse wave and analyzing the changing component. Further, SpO2 as the oxygen saturation only for the arterial blood can be measured by analyzing the changing component of the two types of lights under irradiation.

Accordingly, the pulse oximeter can measure the SpO2 and the pulse rate simultaneously, which can be utilized for the evaluation of oxygen exchange function in the lung. On the other hand, SpO2 cannot be measured in a portion where arterial pulse cannot be detected.

By the way, in a case of heart surgery, it is necessary to always confirm the cerebral state by measuring the oxygen state in the cerebral cells, specifically, in the cerebral cortex on real time. However, the existent pulse oximeter described above cannot measure the oxygen state in the cerebral cortex.

When a probe of a pulse oximeter is attached to finger tips or earlobes for measuring the SpO2, since the distance between the light emitting unit and the light receiving unit is short, a light emitted from the light emitting unit transmits straight in the tissue of the finger tips or earlobes to the light receiving unit and SpO2 can be measured based on the light absorption amount.

By the way, the cerebral cortex is a thin layer of neuron cells extending over the cerebral surface and the cerebral cortex is covered with scalps, skulls and cerebral spinal fluids. Accordingly, even if it is intended to measure the oxygen state in the cerebral cortex by the pulse oximeter, since the light emitted from the light emitting unit is scattered or diffused due the presence of obstacles such as scalps, skulls, cerebral spinal fluids, etc., the light receiving unit cannot exactly receive the light, so that the oxygen state in the cerebral cortex cannot be measured exactly.

Then, there has been provided a tissue oxygen saturation measuring apparatus capable of measuring the tissue oxygen saturation (hereinafter referred to as "rSO2") by setting the probe to a desired position, for example, of a forehead as in the pulse oximeter (for example, refer to Japanese Patent Laid-Open No. 2006-75354).

The probe adapted to be used for the tissue oxygen saturation measuring apparatus comprises a light emitting unit that emits light of two types of near infrared lights at different wavelengths and a light receiving unit that receives the light emitted from the light emitting unit. The probe is attached to a desired position such as on a forehead, in which the light emitting unit and the light receiving unit are fixed at a predetermined distance on one identical plane being directed to an identical direction. The probe is set to a desired position of the forehead or the like and the light receiving unit receives two types of lights emitted from the light emitting unit and rSO2 can be measured by analyzing the received light.

In the tissue oxygen saturation measuring apparatus, since the tissue oxygen saturation is calculated for all the lights received by the light receiving unit by arithmetic means, the measured oxygen saturation is the oxygen saturation for the entire blood contained in the peripheral vessels of the target tissue, and the oxygen saturation measured by the tissue oxygen saturation measuring apparatus generally shows measured values containing 25% arterial ingredient and 75% venous ingredient.

Since rSO2 measured by the tissue oxygen saturation measuring apparatus includes a lot of information of venous blood after transferring oxygen through capillary vessels to the tissue, this is utilized for evaluation whether oxygen is supplied sufficiently to the tissue or not and, further, whether the oxygen metabolism is performed normally or not. Particularly, this provides important index for evaluation upon heart surgery or the cerebral oxygen state of patients suffering from cardiac arrest. On the other hand, since the arterial information is less detected, the tissue oxygen saturation measuring apparatus cannot measure the pulse rate or SpO2 exactly.

While the pulse oximeter and the tissue oxygen saturation measuring apparatus described above measure the oxygen saturation in the same manner, since targets to be measured are different respectively, they are optionally utilized selectively or simultaneously in parallel in the medical field depending on the values intended to be measured.

SUMMARY OF THE INVENTION

However, equipment such as pulse oximeters and tissue oxygen saturation measuring apparatus also had inherent problems respectively. First, the pulse oximeter involves a problem of low temperature burns upon measurement of SpO2 by using probes for a long time.

Change in the thickness due to the pulse wave occurs in an extremely short time and, in order to detect the pulse wave by the pulse oximeter, it is necessary for the light emitting unit to emit light to the tissue at a pulse rate of 30/sec. or more.

Since the light emitted from the light emitting unit is near infrared light, i.e., heat ray, when the SpO2 is measured by a pulse oximeter continuously at an identical portion, thermal accumulation is caused by near infrared light to result low temperature burns. Accordingly, long time setting of a probe to an identical portion is specified as a contraindication or inhibitive matter in the pulse oximeter.

In order to prevent low temperature burns in SpO2 measurement by the pulse oximeter, it is necessary to periodically change the setting position of the probe. However, since this requires reliable management for setting time or change of the setting position, this may be time consuming and increase human costs.

On the other hand, the tissue oxygen saturation measuring apparatus involves a problem of taking much time for setting the amount of light emitted from the light emitting unit depending on the portion of the target tissue to be measured. Specifically, in the probe utilized for the tissue oxygen saturation measuring apparatus, since the light emitting unit and the light receiving unit are situated at a predetermined distance and the distance between the light emitting unit and the light receiving unit has to be 1.25 times to 1.5 times the depth from the epidermis on which the probe is set.

The oxygen saturation of the target tissue is measured by a probe in which a light emitting unit and a light receiving unit are situated at a distance corresponding to the target tissue to be measured optionally. If the amount of light emitted from the light emitting unit is excessive, relative to the depth where the target tissue is present, this causes a phenomenon identical with halation in photography in which the periphery of a subject becomes blurred and unclear due to excess amount of light, so that the change of the hemoglobin oxygen saturation can no more be measured.

In order to accurately measure the oxygen saturation on the target tissue without causing such halation, since a light absorbance amount optional to the distance between the light emitting unit and the light receiving unit is present, it is necessary to control the amount of light emitted from the light emitting unit so that the change of the oxygen saturation of hemoglobin can be measured relative to the depth of the target tissue to be measured from the epidermis, that is, relative to the distance between the light emitting unit and the light receiving unit.

In a case where the target tissue to be measured situates deeply from the epidermis, it is necessary to increase the amount of light emitted from the light emitting unit and, on the other hand, in a case where the target tissue to be measured situates at a shallow place from the epidermis, halation would be caused unless the amount of light to be emitted from the light emitting unit is decreased, failing to measure the change of the oxygen saturation of hemoglobin.

Conversely, when less amount of light is emitted from the light emitting unit in a case where the target tissue to be measured situates deeply from the epidermis, the light receiving unit cannot accurately receive light, failing to measure the change of the oxygen saturation of hemoglobin.

Further, when the distance between the light emitting unit and the light receiving unit is different depending on the depth of the target tissue to be measured, since the ratio of light loss is different due to light scattering or diffusion, this takes a considerable time for controlling the exact amount of light.

Further in the medical field, patient's SpO2 or rSO2 has sometimes to be measured for a long time. In such a case, rSO2 cannot be measured accurately by a pulse oximeter used for measuring SpO2 as described above, whereas SpO2 cannot be measured accurately by a tissue oxygen saturation measuring apparatus for measuring rSO2, so that the pulse oximeter and the tissue oxygen saturation measuring apparatus have to be provided separately for measuring SpO2 and rSO2 respectively, which requires much installation cost.

The present invention has been accomplished in view of the foregoings and it intends to provide an oxygen saturation measuring apparatus, and a probe adapted to be used therefor capable of measuring arterial oxygen saturation (SpO2) and tissue oxygen saturation (rSO2) safely, easily and economically at a desired position of a biological body for a long time continuously.

In order to solve the foregoing problems, the present invention provides an oxygen saturation measuring apparatus for measuring oxygen saturation of a biological body by measuring near infrared light emitted from a light emitting unit to a biological body and measuring the same by a light receiving unit comprising;

an information storage device provided corresponding to the depth of a target to be measured for tissue oxygen saturation for storing a distance information between the light emitting unit and the light receiving unit, a light emission driving unit for making the light emitting unit emit light in an amount of light corresponding to the distance information, a pulse outputting unit for outputting pulse capable of measuring the tissue oxygen saturation, and a pulse increasing unit for increasing the rate of pulses from the pulse outputting unit for a predetermined time thereby allowing measurement of arterial blood oxygen saturation.

Thus, the information storage device stores information relevant to distance between the light emitting unit and the light receiving unit provided corresponding to the depth of a target to be measured for the tissue oxygen saturation, the light emission driving unit drives the light emitting unit emit light by a light amount corresponding to the distance information, the pulse outputting unit makes the light emitting unit emit pulses capable of measuring tissue oxygen saturation, and the pulse increasing unit increases the pulse amount from the pulse outputting unit to the pulses capable of measuring the arterial oxygen saturation for a predetermined time.

Further, the present invention provides a probe adapted to be used in an oxygen saturation measuring apparatus for measuring near infrared lights emitted from light emitting unit to a biological body by the light receiving unit comprising;

an information storage device provided corresponding to the depth of an object to be measured for the tissue oxygen saturation for storing information relative to distance between the light emitting unit and the light receiving unit, a light emission driving unit for driving the light emitting unit emit an amount of light corresponding to the distance related information, and a pulse outputting unit for making a light emitting unit to emit light in an amount of light corresponding to the distance related information.

Thus, the information storage device stores the distance related information for the light emitting unit and the light receiving unit provided corresponding to the depth of the target to be measured for the tissue oxygen saturation, the light emission driving unit drives the light emitting unit emit light by a light amount corresponding to the distance related information, and the pulse outputting unit applies the light emitting unit with pulses capable of measuring the tissue oxygen saturation.

Further, the present invention provides a method of measuring an oxygen saturation of measuring the oxygen saturation in a biological body by measuring a near infrared light applied from a light emitting unit to the biological body at a light receiving unit, the method including;

a step of storing a distance related information for the light emitting unit and the light receiving unit provided corresponding to the depth of a target to be measured for the tissue oxygen saturation, a step of emitting a light from the light emitting unit in an amount of light corresponding to the distance related information by a light emission driving unit, a step of applying pulses capable of measuring the tissue oxidation saturation to the light emitting unit by a pulse outputting unit and a step of increasing the amount of the pulses from the pulse outputting unit to pulses capable of measuring the arterial oxygen saturation for a predetermined time by a pulse increasing unit.

Thus, the information storage device stores distance related information (hereinafter, sometimes referred to also as distance information) for the light emitting unit and the light receiving unit provided at a distance corresponding to the depth of the target to be measured for the tissue oxygen saturation, the light emission driving unit makes the light emitting unit emit light in an amount of light corresponding to the distance related information, the pulse outputting unit applies the pulses capable of measuring the tissue oxygen saturation to the light emitting unit, and the pulse increasing unit increases the amount of pulses from the pulse outputting unit for a predetermined time to pulses capable of measuring the arterial oxygen saturation.

According to the oxygen saturation measuring apparatus, the probe, and the oxygen saturation measuring method of the present invention, since the information storage device stores the distance information between the light emitting unit and the light receiving unit provided corresponding to the depth of the target to be measuring for the tissue oxygen saturation, the light emission driving unit makes the light emitting unit emit a light in an amount of light corresponding to the distance information, the pulse outputting unit makes the light emitting unit emit pulses capable of measuring the target tissue saturation and the pulse increasing unit increases the amount of pulses from the pulse outputting unit for a predetermined time to pulses capable of measuring the arterial blood oxygen saturation. Accordingly, since heat accumulation in the tissue due to the near infrared light is mitigated and since a single apparatus can measure both SpO2 and rSO2, the arterial blood oxygen saturation (SpO2) and tissue oxygen saturation (rSO2) can be measured safely, easily and economically at a desired position on the biological body for a long time continuously.

DETAILED DESCRIPTION OF PREFERRED EMBODIMENTS

Figure 1A:
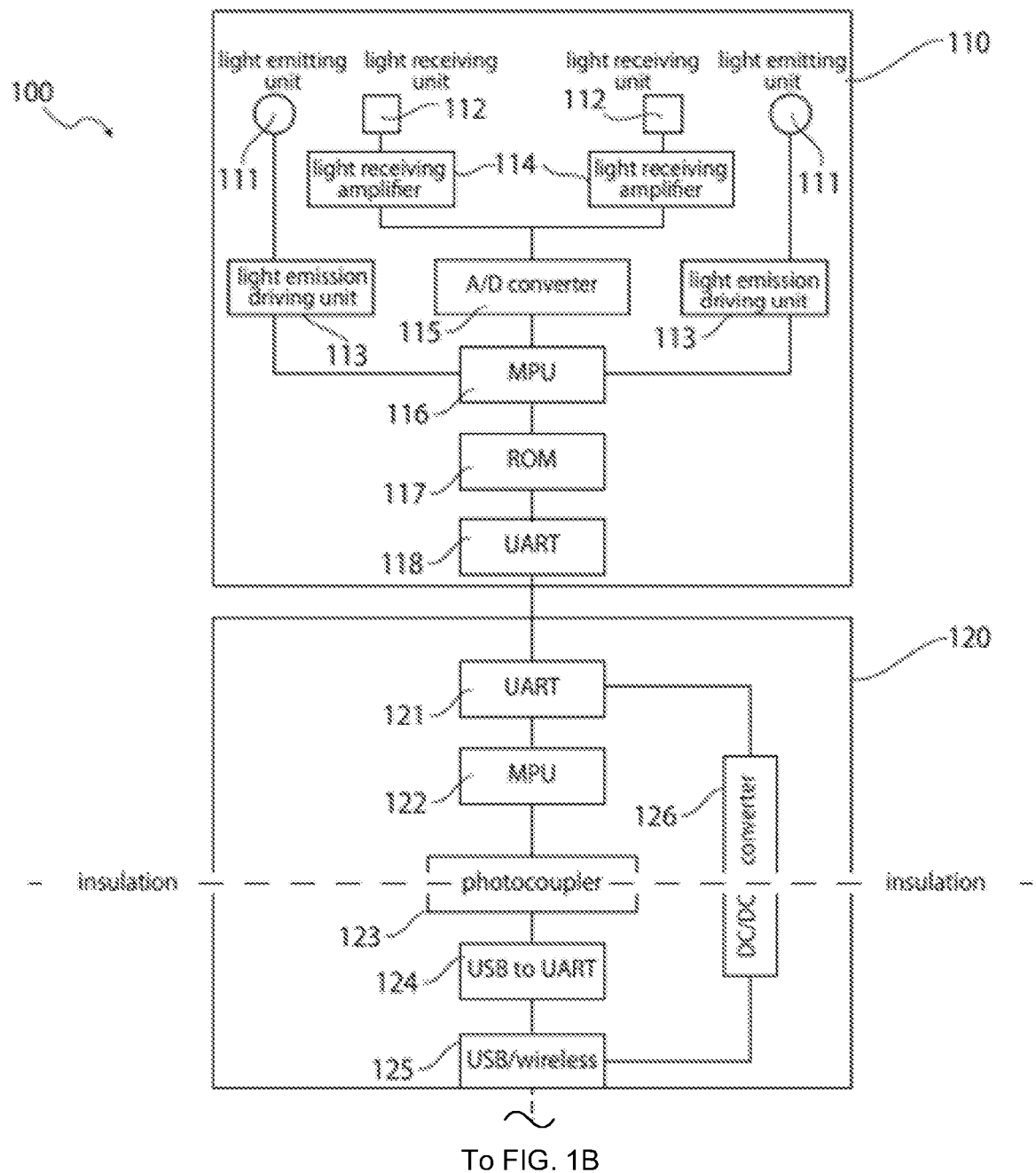
FIGS. 1A and 1B are a block diagram illustrating an entire configuration of an oxygen saturation measuring system according to the present invention.
Figure 1B:
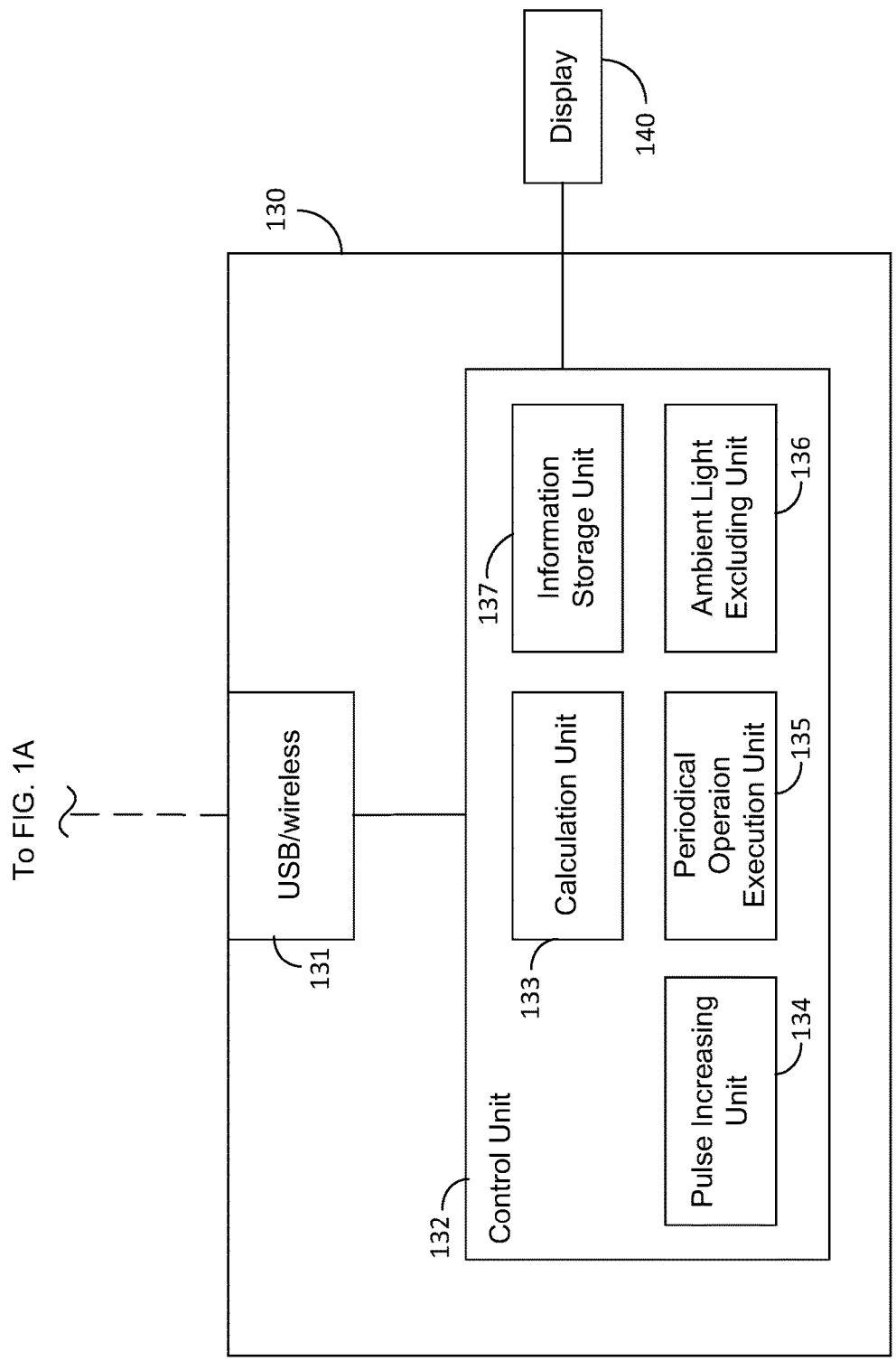

Preferred embodiments of the present invention are to be described specifically with reference to the drawings. FIGS. 1A and 1B are a block diagram illustrating an entire configuration of an oxygen saturation measuring apparatus (sometimes referred to also as a system) according to the present invention. As shown in FIGS. 1A and 1B are, the oxygen saturation measuring system 100 includes a probe 110, an apparatus main body 120, a terminal equipment 130 and a display 140.

The probe 110 is adapted to be set to a biological body for obtaining information of a target tissue, so that the information obtained by way of the apparatus main body 120 can be digitalized and sent to the terminal equipment 130.

The apparatus main body 120 is adapted to operate the probe 110 by sending signals to the probe 110 and relay and send the digital signals obtained from the probe 110 to the terminal equipment 130.

The terminal equipment 130 is adapted to perform arithmetic operation of calculating, for example, the oxygen saturation of a target tissue measured by the probe 110 based on the information obtained from a target tissue obtained by way of the apparatus main body 120 for storing the result thereof.

The display 140 is adapted to display information, graph, etc. of the oxygen saturation calculated by the terminal equipment 130, which is a monitor connected with the terminal equipment 130. Further, the display 140 can display also a menu screen, etc. of selecting an instruction for operating the probe 110 or the apparatus main body 120.

Further, the oxygen saturation measuring system 100 can measure the oxygen saturation of a target tissue, process the measured data, control such as starting and ending of the system, and supply electric power to the probe 110, the apparatus main body 120, etc. by the operation using the terminal equipment 130 and the display 140.

The probe 110 is a detector set to a portion of a biological body and adapted to measure the oxygen saturation of a target tissue intended to obtain information, and includes a light emitting unit 111, a light receiving unit 112, a light emission driving unit 113, a light receiving amplifier 114, an analog-digital converter 115 (hereinafter referred to as A/D converter 115), a MPU (Micro Processing Unit) 116, a ROM (read-only memory) 117 (hereinafter also referred as an information storage unit), and a UART (Universal Asynchronous Receiver Transmitter) 118.

The light emitting unit 111 is adapted to obtain information of the target tissue intended to be obtained by application of lights as plural types of near infrared lights to a biological body and includes, for example, near infrared light emitting diodes at three wave lengths as an optical source of light emission.

The near infrared light emitting diodes at three wavelengths of the light emitting unit 111 are, for example, near infrared light emitting diodes at wavelengths of 770 nm, 805 nm and 870 nm. Such near infrared light emitting diodes are connected respectively to the light emission driving units 113.

The light receiving units 112 are adapted to detect light emitted from the light emitting unit 111 and connected respectively to the light receiving amplifiers 114. The light receiving unit 112 is, for example, a photodiode and can output light in a sensitivity region thereof as a signal irrespective of the wavelength of light emitted from the light emitting unit 111.

The light emitting unit 111 and the light receiving unit 112 are provided at a predetermined distance and can measure the change of hemoglobin in the target tissue situated to a depth which is within 70% to 80% of the distance depending on the distance between the light emitting unit 111 and the light receiving unit 112.

A plurality of probes 110 each having an optional distance between the light emitting unit 111 and the light receiving unit 112 are provided, from which a desired probe 110 can be selected and utilized depending on the position of the target tissue intended to be measured. Further, while it is necessary that the light emitting unit 111 emits an appropriate amount of light relative to the distance between the light emitting unit 111 and the light receiving unit 112. The control method is to be described later.

The light emission driving unit 113 is adapted to emit light from the light emitting unit 111 and includes, for example, a transistor that controls the current for emitting light from the near infrared light emitting diode at a constant current, and connected with the light emitting unit 111 and the MPU 116.

The light emitting unit 111 can emit intense light of a larger amount and can send the light as far as a target tissue at a deep position of a biological body by increasing the current supplied from the light emission driving unit 113.

The light receiving amplifier 114 is adapted to amplify the received optical signals detected by the light receiving unit 112 to a necessary signal level and connected with the light receiving unit 112 and the A/D converter 115.

The A/D converter 115 is adapted to convert analog signals into digital signals and connected with the light receiving amplifier 114 and the MPU 116. The light receiving amplifier 114 amplifies received optical analog signals detected by the light receiving unit 112 and the A/D converter converts the amplified received optical analog signals into digital signals.

In the prior art, the light emitted from the light emitting unit 111 was received by the light receiving unit 112, which was amplified by the light receiving amplifier 114 and the light receiving amplifier 114 transferred the analog signals at a low voltage amplified by the light receiving amplifier 114 by way of a communication cable, for example, to terminal equipment, etc., placed several meters ahead.

By the way, the analog signals at a low voltage are liable to undergo the effect of external noises, so that measured values are instable. Then, in the present invention, the light emitted from the light emitting unit 111 is received by the light receiving unit 112, and analog signals amplified by the light receiving amplifier 114 are amplified to a necessary signal level and, just thereafter, the A/D converter 115 converts the analog signals into digital signals.

Thus, analog signals liable to undergo the effect of external noises are not transmitted in the communication cable but, instead, stable signals converted by the A/D converter 115 can be transmitted as digital signals.

The MPU 116 is a microprocessor for controlling each of connected equipment and connected with the light emission driving unit 113, the A/D converter 115, and the ROM 117. For example, the light emission driving unit 113 makes the light emitting unit 111 emit light at pulses in synchronous with the clock pulses from the MPU 116.

The ROM 117 is an information storage device for storing information. For example, it stores calibration data for the output of the light receiving amplifier 114, which is a coefficient for calibrating the output of the light receiving amplifiers 114 for making the signal levels of analog signals outputted from the light receiving amplifiers 114 equal to each other.

The light emitting unit 111 may comprise near infrared light emitting diodes at a plurality of different wavelengths. A current required for emitting light from each of near infrared light emitting diodes is different. Further, even if the infrared light emitting diodes are driven to emit light by an identical current, the optical output is different depending on the individual difference of the infrared light emitting diodes. Accordingly, light signals at each of wavelengths received by the light receiving unit 112 is also different and the signal levels of the analog signals outputted from the light receiving amplifiers 114 are also different.

Then, by previously storing the coefficient for calibrating the signal levels outputted from the light receiving amplifiers 114 in the ROM 117 when each of near infrared light emitting diodes emits light at a constant current such that the signal levels outputted from the light receiving amplifiers 114 are identical, when the hemoglobin absorbance is determined subsequently from the signal levels, absorbance determined from the absorption coefficient of hemoglobin can be made identical based on the light applied from the near infrared light emitting diode at each wavelengths.

Thus, even if imbalance or variation should be caused to the sensitivity of the light emitting unit 111 and the light receiving unit 112 used for the probe 110, such imbalance or variation in the sensitivity of the light emitting unit 111 and the light receiving unit 112 is calibrated, so that change of hemoglobin can be measured accurately, and the oxygen saturation of the target tissue can be measured accurately.

For the light emitting unit 111 and the light receiving unit 112 used in the probe 110, mass produced devices such as near infrared light emitting diodes or photodiodes are used. However, characteristics of such devices, for example, light emitting outputs and light receiving sensitivity are not quite identical but imbalance or variation may be caused.

Then, by previously storing, in the ROM 117, phantom-based calibration data as reference values with respect to the transmission light measured previously by using phantoms capable of obtaining absorption characteristics identical with those of biological bodies to be described later, even if imbalance or variation should be caused to the sensitivity of the light emitting unit 111 and the light receiving unit 112 used in the probe 110, imbalance and variation in the sensitivity of the light emitting unit 111 and the light receiving unit 112 are calibrated, change of hemoglobin can be measured accurately, and the oxygen saturation of the target tissue can be measured.

Specifically, voltage data for the ratios of the light wavelengths different in the light emitting unit 111 in which the oxygen saturation is at 50% on the phantom are stored in the ROM 117. Further, the data for amplification factor of the light receiving amplifiers 114 can also be stored.

Further, the ROM 117 can also store the distance information between the light emitting unit 111 and the light receiving unit 112 and the voltage information for applying an appropriate amount of light relative to the distance between the light emitting unit 111 and the light receiving unit 112. The light emitting unit 111 can omit light to the biological body based on the voltage information.

A UART (Universal Asynchronous Receiver/Transistor) 118 is adapted to send and receive signals obtained in the probe 110 for transmitting to the apparatus main body 120 and the signal for operating the probe 110, and connected detachably and exchangeably with the apparatus main body 120 by a communication cable.

As described above, in the probe 110, the distance between the light emitting unit 111 and the light receiving unit 112 is different depending on the depth where the target tissue for which information is intended to be obtained and an optional probe 110 can be selected and used depending on the position of the target tissue intended to be measured. During measurement, the selected probe 110 is set to the apparatus main body 120 for measurement.

Thus, since the probe 110 which is used being in contact with the biological body is exchangeable, only the probe 110 to be in contact with the biological body can be made disposable to improve health and safety.

The apparatus main body 120 is attached with the probe 110 selected depending on the depth of the target tissue to be measured and adapted to operate the probe 110 by sending signals to the probe 110, and relay and send the digital signals obtained from the probe 110, and comprises UART, MPU 122, Photo Coupler 123, USB (Universal Serial Bus) to UART 124, USB interface 125 and DC/DC converter (Direct Current Converter).

The UART 121 is adapted to send and receive signals obtained from the probe 110 to the apparatus main body 120 and signals for operating the probe 110, and is connected detachably and exchangeably by way of communication cables to the probe 110.

The MPU 122 is a microprocessor adapted to control each of connected instrument, and connected with the UART 121 and the Photo Coupler 123. The Photo Coupler 123 is adapted to once convert electric signals into light signals therein and then return them again to electric signals for transmitting the signals under electric insulation, which is connected with the MPU 122 and the USB to UART 124. Thus, the probe 110 in contact with the biological body and the terminal equipment 130 are insulated to satisfy the conditions used as medical equipment.

The USB to UART 124 are a conversion module for converting signals sent from the Photo Coupler 123 into a form adaptable to a USB interface 125, and connected with the Photo Coupler 123 and the USB interface 125.

The USB interface 125 is a connector for connecting the apparatus main body 120 by way of a communication cable such as a USB cable to the terminal equipment 130. Thus, the apparatus main body 120 is connected by way of the USB cable with the terminal equipment 130.

The DC/DC converter 126 is adapted to provide a power source for supplying electric power from the terminal equipment 130 connected by way of the USB cable to the probe 110 and connected with the USB interface 125 and the UART 121.

The terminal equipment 130 is adapted to perform calculation operation of calculating the oxygen saturation, etc. of a target tissue measured by the probe 110 from the information of a target tissue obtained by way of the apparatus main body 120, and stores the result thereof. The terminal equipment 130 comprises a USB interface 131 and a control unit 132.

The USB interface 131 is a connector adapted to connect the terminal equipment 130 by way of a communication cable such as a USB cable to the apparatus main body 120, and connected with the apparatus main body 120 and the control unit 132. Thus, the terminal equipment 130 is connected by way of the USB cable to the apparatus main body 120.

The control unit 132 is adapted to control the operation of the probe 110 connected by way of the apparatus main body 120, and connected with the USB interface 131 and a display 140.

Further, the control unit 132 can receive the information measured by the probe 110 by way of the apparatus main body 120, calculate and then output the calculated information to a display 140 connected therewith. Specifically, the control unit 132 comprises a calculation unit 133, a pulse increasing unit 134, a periodical operation execution unit 135, an ambient light excluding unit 136, and an information storage unit 137.

The calculation unit 133 is adapted to calculate the oxygen saturation mainly based on the Lambert-Beer's law. This is also adapted to calibrate information based on the calibration data stored in the ROM 117 of the probe 110.

Further, the calculation unit 133 can also calculate relative values of the hemoglobin amount (HbI), the oxygen metabolic amount in the target tissue, etc. based on the information obtained for measuring rSO2 or SpO2. A specific calculation method for the oxygen metabolic amount in the target tissue can be calculated by the following formula 1.

$$\text{Oxygen metabolic amount (CMRO2)} = HbI \times (SpO2 - rSO2) \quad \text{[Formula 1]}$$

The pulse increasing unit 134 is adapted to increase the pulse rate to the light emitting unit 111 of the probe 110 connected by way of the apparatus main body 120 based on the instruction information inputted by a not-illustrated input means.

In the oxygen saturation measuring system 100, the light emitting unit 111 emits light to a biological body usually at pulses capable of measuring rSO2 upon measurement of the oxygen saturation in the target tissue (hereinafter referred to as rSO2 mode). Specifically, in the rSO2 mode, the light emitting unit 111 emits a light at a pulse rate of 10 or less per sec to a biological body. Accordingly, since a light at a low pulse rate is applied to the biological body, no heat accumulation is caused, and rSO2 can be measured with no worry of low temperature burns.

Further, since the light receiving unit 112 can obtain information at an instance by adapting the intensity of the light emitted from the light emitting unit 111 to such an intensity that the change thereof can be detected by the light receiving unit 112, the light emitting time from the light emitting unit 111 can be made as short as about 0.1 mm sec and by sample holding the obtained information and holding the last time data to the next pulse, data processing can be facilitated.

In the pulse increasing unit 134, the pulse rate in the rSO2 mode described above is increased temporarily and the light emitting unit 111 emits light to the biological body at a pulse capable of measuring the SpO2 as in the pulse oximeter (hereinafter referred to as SpO2 mode). Specifically, in the SpO2 mode, the light emitting unit 111 emits light to the biological body at a pulse rate of 30 or more per one sec.

Heat accumulation by near infrared light can be prevented by restricting the irradiation time in the SpO2 mode to about one minute at the maximum. Since the heat accumulation is decreased, SpO2 can be measured with no worry of low temperature burns. Thus, the oxygen saturation measuring system 100 can perform measurement only by one probe 110 attached to the biological body while switching measurement between SpO2 and rSO2.

A periodical operation execution unit 135 is adapted to periodically increase the pulse rate by the pulse increasing unit 134. For example, the periodical operation execution unit 135 operates the pulse increasing unit 134 at a predetermined interval, for example, of 10 minutes. Thus, the light emitting unit 111 can be periodically put to sampling pulse application in the SpO2 mode thereby enabling to measure SpO2. The interval of executing the sampling operation by the periodical operation execution unit 135 may be preferably restricted to about 5 minutes at the least since there is a worry of heat accumulation to the tissue by near infrared light.

Although not illustrated, in the control unit 132, a rSO2 monitoring unit for monitoring the rSO2 state in the rSO2 mode may also be provided and, when the rSO2 is lowered, the rSO2 monitoring unit may switch the pulse increasing unit 134 to the SpO2 mode.

Thus, since the operation mode is automatically switched to the SpO2 mode when rSO2 is decreased and heart arrest is estimated if the pulse wave is not measured, so that an alarm (e.g., an audible or visual alarm) can also be generated, for example, from warning device such as a light or speaker. In another embodiment, the alarm can be in the form of a message or notification provided to a user.

An ambient light excluding unit 136 is adapted to exclude intense ambient light. Heretofore, in the measurement by light such as near infrared light, since the light receiving unit 112 cannot accurately detect light because of intrusion of intense ambient light, measurement is performed mainly in an operation room, ICU, ward, etc. in a hospital, and outdoor measurement is not performed in particular.

Further, while measurement is often performed indoors, actual measurement is not conducted in a completely dark circumstance. The light receiving unit 112 of the probe 110 that receives the light outputs the light as a signal so long as the light is in a sensitivity region irrespective of the wavelength. That is, if it is intended to obtain only the necessary signal applied from the light emitting unit 111, the ambient light is also detected by way of the biological body on the light receiving unit 112.

Then, the ambient light excluding unit 136 first utilizes the information obtained by the light receiving unit 112 during lightless state in which the light emitting unit does not emit light from among the pulses emitted from the light emitting unit 111. Specifically, in the rSO2 mode, the light emitting unit 111 gives 4 types of optical states, that is, lightless state or light emission states at 770 nm, 805 nm, and 870 nm, the light receiving unit 112 receives such 4 types of lights and stores the signals in the information storing unit 137 at 1 to 5 sec moving average, which is utilized for the calculation in the calculation unit 133.

During the lightless state in which the light emitting unit 111 does not emit light, the light received by the light receiving unit 112 depends on the measuring circumstance. In a case where measurement is performed in a bright place such as outdoors, bright ambient light is received by the light receiving unit 112 by way of a biological body. In a case where the measurement is performed indoors in a dark room, a slight light in the dark room is received by way of the biological body to the light receiving unit 112. They are referred to as ambient light signals.

Since signals attributable to the ambient light already enter the light receiving unit 112, when the light emitting unit 111 emits light, the light receiving unit 112 detects ambient light increased by light emission from the light emitting unit 111.

That is, a necessary light to be measured by the light receiving unit 112 is a difference between the light detected by the light receiving unit 112 and the ambient light, and the necessary light signal to be measured by the light receiving unit 112 can be obtained as the received light signal minus ambient light signal at the light receiving unit 112.

In the ambient light excluding unit 136, a light signal excluding the ambient light can be obtained by such processing. Further, the probe 110 is set to the epidermis of the target tissue during measurement and the light receiving unit 112 is shielded from the ambient light. Then, an ambient light monitoring unit for monitoring the external signal is provided and when the external signal monitored by the ambient light monitoring unit is higher than a usual level of the ambient light, it can be judged that the probe 110 and, in particular, the light receiving unit 112 falls off the epidermis and an alarm (e.g., an audible or visual alarm) can also be generated, for example, by a warning device such as a light or speaker. In another embodiment, the alarm can be in the form of a message or notification provided to a user.

The information storage unit 137 can also store the result of calculation by the calculation unit 133 and can also store the ambient light signal utilized by the ambient light excluding unit 136, and is adapted for storing various information.

While it has been explained above that the apparatus main body 120 and the terminal equipment 130 are connected by the USB interface 125 and the USB interface 131 by way of the USB cable, the USB interface 125 and the USB interface 131 may also be connected by wireless communication devices, e.g., transceivers, transmitters, receivers, antennas, etc., that can communicate not by way of wired cables such as communication cables.

Thus, connection portions between each of the equipment by way of the wired communication cables can be decreased, thereby capable of decreasing accidents to monitors or the like by entangling hands or legs during movement and therapeutic operation of patients.

Further, FIGS. 1A and 1B show a double type configuration in which light emitting units 111 and the light receiving units 112 are provided in right and left pair to the probe 110 but the number and the positions of them may be changed optionally.

For example, a single type configuration may be used in which a light emitting unit 111 is provided on one side and a light receiving unit 112 is provided on the other side with respect to the center of the probe 110. In a case of the single type configuration, the single type probe 110 is attached to other desired different positions of the biological body.

In the probe 110, since channels each comprising a set of plural light emitting units 111 and light receiving units 112 are usually used simultaneously (generally, two left and right channels on the forehead portion), if the plural light emitting units 111 and the light receiving units 112 operate simultaneously, signals interfere each other making it impossible to distinguish the derivation source of the signals.

Then, it is preferably controlled such that the light emitting units 111 and the light receiving units 112 of the probe 110 operate independently with no interference with respect based on the clock pulses from the MPU 116 as a reference. Thus, the number of communication cables connected to the probe 110 can be decreased compared with the case of connection using analog signals.

Then, a method of measuring the oxygen saturation by using the oxygen saturation measuring system 100 is to be described. First, a probe 110 corresponding to the depth of a target tissue to be measured is selected and connected to the apparatus main body 120, and the probe 110 is set to the epidermis of the target tissue to be measured.

Then, number of channels to be measured and the measuring conditions are designated from the menu screen by using the terminal equipment 130 and the display 140, and a measuring start button is turned on. The apparatus main body 120 reads information from the ROM 117 in the connected probe 110.

Control pulses are outputted from the apparatus main body 120 to the probe 110 based on the information obtained from the ROM 117, and the light emitting unit 111 emits light in an amount corresponding to the control pulse in the probe 110 to apply light to a biological body.

The lights applied to the biological body, upon passing through the capillary bed in the biological body, are absorbed to oxyhemoglobin and deoxyhemoglobin and are converted into analog electric signals in the light receiving unit 112 as signals showing absorption which is different on every wavelength.

The converted analog signals are converted by the A/D converter 115 to digital signals, outputted from the probe 110, and then sent by way of the apparatus main body 120 to the terminal equipment 130.

In the terminal equipment 130, oxygen saturation of the target tissue is calculated by the control unit 132, and the processed calculation result is displayed on the display 140 and, at the same time, stored in the terminal equipment 130. Further, graphic information such as a trend graph can also be displayed on the display 140. Usually, rSO2 is measured in the rSO2 mode and SpO2 is measured optionally or periodically.

Figure 2:
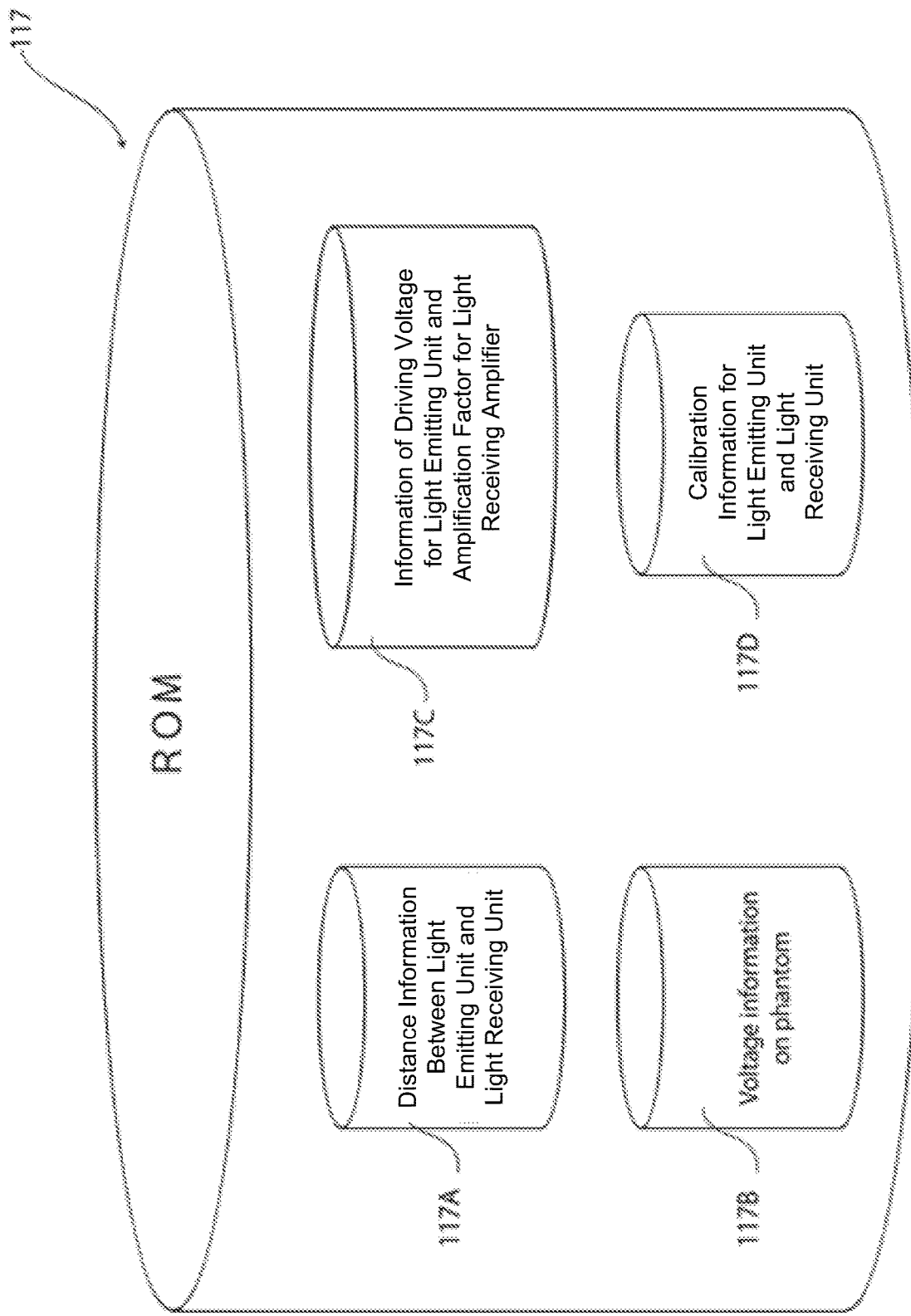
FIG. 2 is a block diagram illustrating examples of information stored in a ROM.

FIG. 2 is a block diagram illustrating examples of the information stored in a ROM (Read Only Memory; sometimes also referred to as an information storage device). As shown in FIG. 2, the ROM 117 stores distance information 117A between the light emitting unit 111 and the light receiving unit 112, voltage information 117B for the ratio of different light wavelengths of light emitting unit 111 where the oxygen saturation is at 50% on the phantom, information 117C of the driving voltage of the light emitting unit 111 and the amplification factor of the light receiving amplifier 114, and calibration information 117D for the light emitting unit 111 and the light receiving unit 112. As the distance information 117A between the light emitting unit 111 and the light receiving unit 112, distance information between the light emitting unit 111 and the light receiving unit 112 which are set depending on the depth of the target tissue to be measured are stored.

As the voltage information 117B for the ratio of different light wavelengths in the light emitting unit 111 in which the oxygen saturation is 50% on the phantom for calibrating the probe 110, voltage information for the ratio of the different light wavelengths is stored in the light emitting unit 111 in which the oxygen saturation is 50% on the phantom as the reference.

(Calibration by Phantom)

Since devices used, for example, in the light emitting unit 111 and the light receiving unit 112 are mass produced, their characteristics such as light emitting output and light receiving sensitivity are not quite identical with each other but give imbalance or scattering individually. Calibration for characteristics are necessary in order to use such devices for the probe 110. Otherwise, accurate measuring values cannot be attained. Then, in the oxygen saturation measuring system according to the present invention, they are calibrated by utilizing phantoms.

Figure 3:
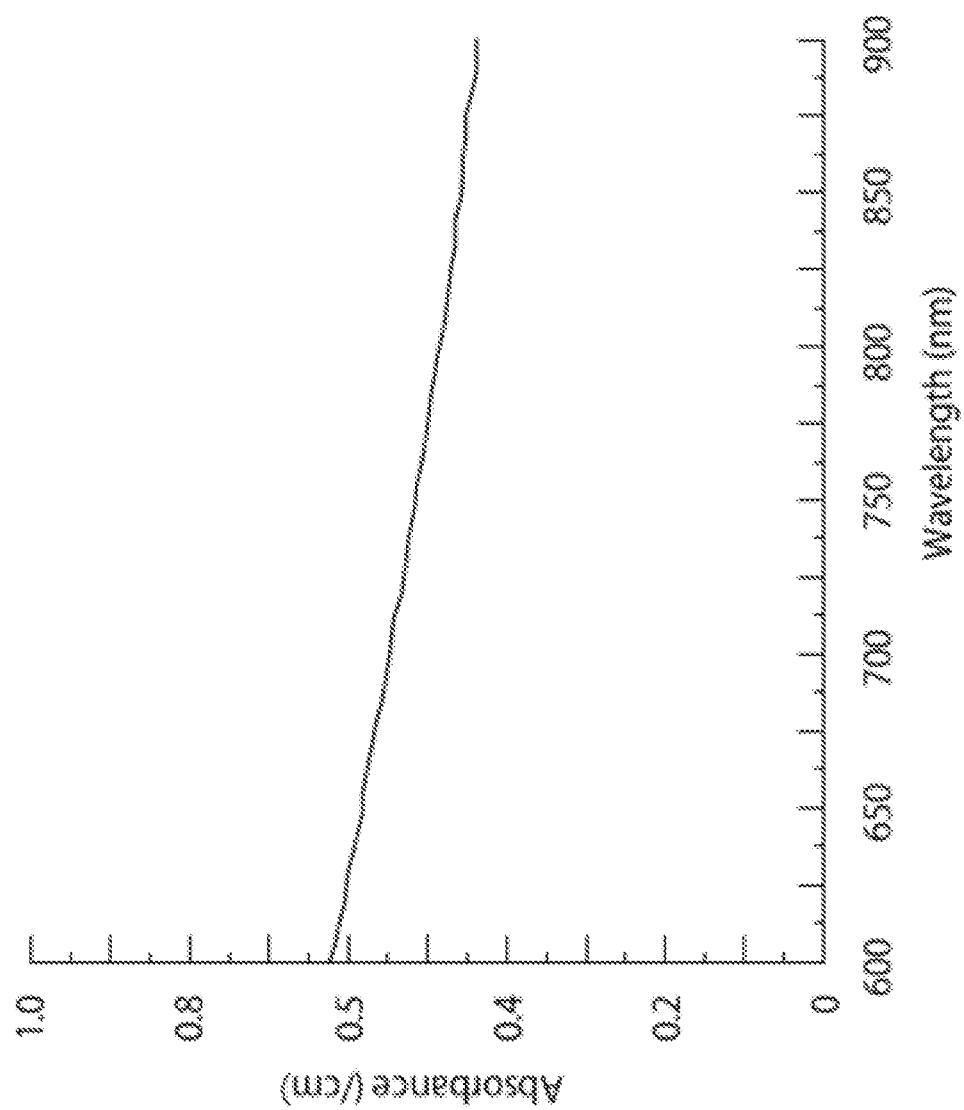
FIG. 3 is a graph showing the result of measuring an absorption coefficient of a resin plate.

FIG. 3 is a graph showing the result of measuring the absorption coefficient of a resin plate. In the present invention, calibration is applied by utilizing a phantom but resin materials having equal absorbance for two types of wavelengths to be used as described above are not present. Accordingly, a material having an absorption coefficient substantially equal between two types of light wavelengths as shown in the result of FIG. 3 is selected and utilized as a reference in the calibration.

As an example of a selected resin plate, a vinyl chloride plate which is grey in appearance and 0.5 mm in thickness is used. FIG. 3 is a graph showing the result of measuring the light absorbance of the grey resin plate by using an absorptiometer.

Absorption coefficients $\varepsilon$ of the grey vinyl chloride resin plate are as shown in the following Table 1.

TABLE 1

| Wavelength | 770 nm | 805 nm | 870 nm |
|---|---|---|---|
| Resin plate light absorption coefficient $\varepsilon$ | 0.51 | 0.49 | 0.42 |

In a case where the amount of oxyhemoglobin in which hemoglobin and oxygen are bonded and the amount of deoxyhemoglobin in which oxygen is detached from oxyhemoglobin are equal, the oxygen saturation is 50%. A method of calibrating the oxygen saturation to 50% when the ratio of the light absorption amount of the two types of light wavelengths (R/IR ratio) on the phantom is 1.0 is performed as below.

For the light absorption coefficients $\varepsilon$ at respective wavelengths, values shown in the following Table 2 are used.

TABLE 2

| Wavelength | 770 nm | 805 nm | 870 nm |
|---|---|---|---|
| K (deoxyhemoglobin) | 0.35 | 0.196 | 0.18 |
| K (oxyhemoglobin) | 0.16 | 0.196 | 0.25 |
| K (resin plate) | 0.51 | 0.49 | 0.42 |

Assuming the light absorbance as K, the light absorption coefficient $\varepsilon$ is represented as $\varepsilon=0.434K$ and shown as in the following Table 3.

TABLE 3

| Wavelength | 770 nm | 805 nm | 870 nm |
|---|---|---|---|
| $\varepsilon$ (deoxyhemoglobin) | 0.368 | 0.451 | 0.576 |
| $\varepsilon$ (oxyhemoglobin) | 0.806 | 0.451 | 0.414 |
| $\varepsilon$ (resin plate) | 1.175 | 1.037 | 0.968 |

According to the Lambert-Beer's law, K=εCd and the light absorbance K at the wavelength λ is represented by the following formula 2.

$$K\lambda=(rSO2 \times KHbO2+(1-rSO2) \times KHb)cd \quad \text{[Formula 2]}$$

The absorbance K for each of the wavelengths (770 nm, 805 nm, 870 nm) used in the oxygen saturation measuring system 100 of the present invention is obtained from the following formulas provided below starting with formulas 3A-3C.

[Formulas 3A-3C]

$$R=K770=(rSO2 \times 0.368+(1-rSO2) \times 0.806)cd \quad (3A)$$

$$IR=K870=(rSO2 \times 0.576+(1-rSO2) \times 0.414)cd \quad (3B)$$

$$R/IR=(0.806-0.438 \cdot rSO2)/(0.414+0.162 \cdot rSO2) \quad (3C)$$

Assuming R/IR=A, it is represented by the following formulas 4A-4B.

[Formulas 4A-4B]

$$A=(0.806-0.438 \cdot rSO2)/(0.414+0.162 \cdot rSO2) \quad (4A)$$

$$A(0.414+0.162 \cdot rSO2)=(0.806-0.438 \cdot rSO2) \quad (4B)$$

When rSO2 is determined therefrom, it is represented by the following formula 5.

$$rSO2=(0.806-0.414A)/(0.438+0.162A) \quad \text{[Formula 5]}$$

In a case where rSO2 changes from 0% to 100%, the theoretical value for A=R/IR is represented by the following formulas 6A-6B.

[Formulas 6A-6B]

0% rSO2, $$(0.806-0.414 \times 1.186A)=0 \quad A=1.64 \quad (6A)$$

100% rSO2, $$(0.438+0.162 \times 1.186A)=(0.806-0.414 \times 1.186A)$$
$$A=0.539 \quad (6B)$$

When the absorbance K is calculated in terms of the wavelength at rSO2=50%, that is, rSO2=0.5, it is represented by the following formulas 7A-7C.

[Formulas 7A-7C]

$$K\lambda=(rSO2 \times KHbO2+(1-rSO2) \times KHb)cd \quad (7A)$$

$$K770=(0.5 \times 0.368+0.5 \times 0.806)cd=0.587cd \quad (7B)$$

$$K870=(0.5 \times 0.576+0.5 \times 0.414)cd=0.495cd \quad (7C)$$

Then, R/IR=A=1.186. In the theoretical value, the absorbance at two wavelengths when rSO2=50% is as described above. Absorbance at R=K770 is 0.587 cd and absorbance at IR=K870 is 0.495 cd and the absorbance for R is larger.

Then, the measured voltage at the wavelength 770 is corrected by multiplying the absorbance ratio of 1.186. Then, the absorbance at K770 is 0.495 cd and at K870 is 0.495 cd, and R/IR ratio is 1:1. By the correction, the measured value by the oxygen saturation measuring system 100 of the present invention is rSO2=50% at R/IR=1, which is identical with the theoretical value.

Since R/IR=A is 1.175/0.968=1.214, the theoretical oxygen saturation of the resin plate is 1.186:1.214, which is substantially equal as 97.7% when compared with the light absorbance ratio of oxyhemoglobin and deoxyhemoglobin, and the value obtained by correction for 1.186 by calibration based on the phantom value as 50% with reference to the resin plate is at an accuracy of 97.7%.

When the correction is performed also for 0% and 100%, each absorbance ratio A=R/IR is as described below and the calculation formula of rSO2 (theoretical value) is represented by the following formula 8.

$$rSO2=(0.806-0.414A)/(0.438+0.162A) \quad \text{[Formula 8]}$$

In a case where A is multiplied by 1.186 for correction and when rSO2 changes from 0% to 100%, the theoretical value for A=R/IR is represented by the following formulas 9A-9B.

[Formulas 9A-9B]

0% rSO2, $$(0.806-0.414 \times 1.186A)=0 \quad A=1.64 \quad (9A)$$

100% rSO2, $$(0.438+0.162 \times 1.186A)=(0.806-0.414 \times 1.186A)$$
$$A=0.539 \quad (9B)$$

The formulas of the calibration curves based on the corrected theoretical values as described above are represented by the following formulas 10A-10B.

[Formulas 10A-10B]

$$A<1 \quad rSO2=100 \times (1.539-A)/1.08 \quad 100 \sim 50\% \quad (10A)$$

$$A>1 \quad rSO2=100 \times (1.64-A)/1.28 \quad 50 \sim 0\% \quad (10B)$$

When the wavelengths of the light used are different, since the absorption coefficients ε to oxyhemoglobin and deoxyhemoglobin at the respective wavelengths are known, the values are applied to ε=0.434K and calculated again.

As described above, since the phantom having the light absorbance scattering characteristics identical with those of the biological body is applicable also to different wavelengths, when it is used at 805 nm, it is possible to use the absorbance by the phantom as a measurement reference for the hemoglobin amount.

As the phantom for providing a reference of the oxygen saturation, a less wavelength dependent structure, for example, a tightly sealed structure against ambient light is formed by using a resin plate having absorption coefficient ($\mu a$=0.15/cm) and scattering coefficient (($\mu s$=10.6/cm) substantially equal with those of a biological body or an adult skull and overlaying them in plurality.

Thus, at the wavelength of near infrared light between 770 nm and 870 nm emitted from the light emitting unit 111, both the scattering coefficient and the diffusion coefficient can be regarded constant. By overlaying such resin to about 30 mm thickness and combining them as resin plates simulating a state where both of the oxyhemoglobin and deoxyhemoglobin are present each in an equal amount, diffusion and scattering states substantially identical with those of the adult skull can be reproduced, which can be used as the reference for the measurement of oxygen saturation and hemoglobin index.

Since "equal absorption for two types of light wavelengths" means that "oxygen saturation corresponds to 50%", the probe 110 can be calibrated by storing R and IR measured values necessary for calibration on the phantom in the ROM 117 and using them as the reference at 50% oxygen saturation.

(Method of Preparing Calibration Data for the Probe 110)

Calibration verification for ensuring the accuracy of the probe 110 produced so far includes a method of preparing a reference phantom in a blood bath but this requires a large scaled equipment and system.

Then, the present invention provides a method of optionally adjusting blood oxygen saturation and calibrating the probe 110 based on the data R, IR for the absorption amount of blood at each of wavelengths obtained by using the probe 110 to be used actually, and a method of correcting imbalance, variation and error caused in the devices used for the probe 110.

First, a blood gas analyzer capable of measuring the oxygen saturation of blood, a cuvette for injecting a blood sample to be served for measurement (thickness of the blood layer from 1 mm to 2 mm), a reducing agent for decreasing the oxygen saturation of the sample blood (sodium hydrosulfite sodium dithionite $Na_2S_2O_4$), a vessel for containing the sample blood, and a syringe for mixing air into the blood are provided.

For approximating the concentration of the blood filled in the cuvette to the maximum concentration in the tissue (cerebral cortex) present in the capillary vessels of the biological body upon actual measurement of 15 g/dL concentration of the whole human blood, the blood is used being diluted to about ⅓ to ⅕ with physiological saline.
(Measuring Method for the Calibrated Value of Oxygen Saturation)

A fresh pig blood is taken, the blood to be measured is filled in a cuvette of 1 mm thickness, and the oxygen saturation is measured in a circumstance shielded from an ambient light. The procedures are as described below.
(Step S1)

The blood is diluted with physiological saline by 3 to 5 times for approximating to the concentration in the capillary bed.
(Step S2)

A reducing agent is added by about 2% by weight to decrease the oxygen saturation as low as possible.
(Step S3)

The blood adjusted for the oxygen saturation is sucked up by a syringe and the oxygen saturation is recorded by a blood gas measuring equipment.
(Step S4)

The blood is filled in the cuvette, the oxygen saturation is measured by the probe 110 and voltage data for R, IR are recorded.
(Step S5)

The oxygen saturation is increased by stirring the blood to be in contact with air.
(Step S6)

The value of the oxygen saturation is measured and recorded by a blood gas measuring equipment.
(Step S7)

The blood is filled in the cuvette, rSO2 is measured by the probe 110, and voltage measured values for R, IR are recorded.

The process from the step S3 to the step S7 is repeated from the low value of the oxygen saturation till oxygen saturation as high as possible. As described above, reference values concealing the transmission light are measured previously by using a phantom capable of obtaining absorption characteristics identical with those of the biological body, or reference values concealing the transmission light are measured previously by using a blood adjusted to an optional oxygen saturation, which can be stored as reference values in the ROM 117.

For the information 117C of the driving voltage in the light emitting unit 111 and the amplification factor in the light receiving amplifier 114, voltage information for applying an appropriate amount of light and an amplification information for amplifying a signal received by the light receiving unit 112 are a necessary signal level relative to the distance between the light emitting unit 111 and the light receiving unit 112 are stored.
(Calculation Method for Light Amount Relative to the Distance Between the Light Emitting Unit 111 and the Light Receiving Unit 112)

The oxygen saturation is 50% when the amount of oxyhemoglobin where hemoglobin and oxygen are bonded is equal with the amount of deoxyhemoglobin where oxygen is detached from hemoglobin.

The calculation formula for the oxygen saturation is generally represented by the following formula 11.

Oxygen saturation=(oxyhemoglobin amount)/(oxyhemoglobin amount+deoxyhemoglobin amount) [Formula 11]

Light absorption to the hemoglobin is different depending on the wavelength of light applied from the light emitting unit 111, and a light at a wavelength of 805 nm shows an absorption coefficient which is equal between oxyhemoglobin and deoxyhemoglobin.

Assuming the concentration as C and the absorption coefficient as c for the medium according to the Lambert-Beer's law, the absorbance K as an amount of absorbed light is represented by the following formulas 12A-12B.

[Formulas 12A-12B]

$$K=\varepsilon Cd \quad (12A)$$

$$C=K/(\varepsilon d) \quad (12B)$$

Further, the absorbance K is represented by the following formula 13 in terms of an incident light which is a light prior to incidence to the medium and a transmission light which is a light after transmission through the medium having a thickness d:

$K$=Log (incident light/transmission light) [Formula 13]

Thus, the medium concentration C can be calculated when absorbance K at two types of light wavelengths can be measured.

The probe 110 can be subjected to necessary calibration by using a reference phantom having an equal concentration (absorbance) between oxyhemoglobin and deoxyhemoglobin. Since the absorbance K is represented by $K=\varepsilon Cd$ as shown in the formula 2, the concentration C of the medium is 50% when the amount of oxyhemoglobin is equal with that of deoxyhemoglobin.

When the concentration C of the medium is determined on each wavelength and when the concentration of oxyhemoglobin is equal with that of deoxyhemoglobin, rSO2 is 50%. The absorption coefficients ε(m·mol/cm) of oxyhemoglobin and deoxyhemoglobin on each light wavelength are as shown in the following Table 4.

TABLE 4

| Wavelength | 770 nm | 805 nm | 870 nm |
| --- | --- | --- | --- |
| Deoxyhemoglobin) | 0.35 | 0.196 | 0.18 |
| Oxyhemoglobin) | 0.16 | 0.196 | 0.25 |

For the absorbance K at two types of light wavelengths, assuming the wavelength at 770 nm as D7 and that at the wavelength of 870 nm as S8 and, when the concentration C of the medium is equal between oxyhemoglobin and deoxyhemoglobin, values for D7 and S8 are rSO2=50%, and represented by the following formula 14. Values for D7 and S8 are determined based on the voltage upon measurement.

$$C(\text{deoxyhemoglobin}) = (D7/0.35) + S8/0.18 \quad [\text{Formula 14}]$$
$$= C(\text{oxyhemoglobin})$$
$$= (D7/0.16) + S8/0.25$$

When the ratio of the light absorption amount at two types of light wavelengths (R/IR ratio) of different voltage values measured for D7 and S8 is 1.0, the oxygen saturation is 50%, the value is stored in ROM 117.

In the pulse oximeter, since it has been known that the ratio of the light absorption at two types of light wavelengths (R/IR ratio) has a correlation with the oxygen saturation, when a calibration curve is prepared based on the ratio of the light absorption amount (R/IR ratio) between two types of light wavelengths obtained in the probe 110 upon measurement and the oxygen saturation SpO2 obtained by a blood gas analyzer in the blood adjusted for the oxygen saturation, the oxygen saturation can be calculated accurately based on the actually measured R/IR ratio.

(Calculation Method for the Hemoglobin Amount)

Referring to the change of the hemoglobin amount, the level of the signal received by the light receiving unit 112 relative to the light at a wavelength of 805 nm is in inverse proportion with the change of the hemoglobin amount. Since the light absorption amount increases as the hemoglobin amount is larger, the signal received by the light receiving unit 112 is weakened to lower the output voltage.

Then, based on the signal level at the start of measurement as a reference, it is considered that the amount absorbed in the hemoglobin is decreased when the signal increases subsequently, and the present amount of hemoglobin can be calculated based on 1.0 upon starting the measurement with the value of signal upon starting measurement as a denominator and the current signal value as a numerator.

Since a sensor is usually set to a subject and a value of a light signal at a wavelength of 805 nm by absorption to hemoglobin just below the sensor is converted into a measured value, the voltage upon starting the measurement is defined as a reference value 1.0.

The extent that the light at a wavelength of 805 nm has been absorbed to the hemoglobin is calculated based on the absorbance $K = \text{Log}$ (incident light/transmission light) according to the Lambert-Beer's law. Since the intensity of light actually entering the biological body cannot be measured in situ, it is calculated assuming that this is about 1,000 times as much as the signal light received by the light receiving unit 112.

(Calculation Method for Oxygen Saturation)

The oxygen saturation is represented by the percentage of oxyhemoglobin based on the entire hemoglobin in terms of a ratio. When the amount of the oxyhemoglobin and that of the deoxyhemoglobin are at a 1:1 ratio, the oxygen saturation is 50%.

Since the absorbance can be determined based on the voltage signals at R=770 nm and at IR=870 nm showing the absorbance of respective lights at two types of the light wavelengths according to the Lambert-Beds law, the amount of the oxyhemoglobin and the amount of the deoxyhemoglobin can be calculated along with a binary linear equation and the oxygen saturation can be calculated further based thereon. It is generally said that the ratio of the absorbance amounts between two types of light wavelengths (R/IR ratio) is correlated with the oxygen saturation, and this constitutes the ground for the calculation in the pulse oximeter.

(Measured Value for rSO2)

Examples of the calibration curves determined based on the measured values obtained through the process from the step S1 to the step S7 are shown by the following Table 5. In the related formula for determining the oxygen saturation based on actually measured values for the ratio between absorbance of two types of light wavelengths (R/IR ratio), it is assumed that the wavelengths used are D7=770 nm and S8=870 nm.

TABLE 5

| Absorbance ratio | R/IR ratio = | $(\text{Log}10(1000/(1.2 \times D7)/\text{Log}10(1000/S8))$ |
| Correction coefficient | A = | $(\text{Log}10(1000/S8)/\text{Log}10(1000/(1.2 \times D7))$ |
|---|---|---|
| rSO2 calculation formula 40 mm | | IF(H5 <= 1,100 × (1.24 − H5)/0.48, 100 × (1.12 − H5)/0.24) |
| rSO2 calculation formula 30 mm | | IF(H5 <= 1,100 × (1.22 − H5)/0.44, 100 × (1.11 − H5)/0.22) |
| rSO2 calculation formula 20 mm | | IF(H5 <= 1,100 × (1.17 − H5)/0.34, 100 × (1.1 − H5)/0.2) |
| rSO2 calculation formula 10 mm | | IF(H5 <= 1,100 × (1.13 − H5)/0.26, 100 × (1.09 − H5)/0.18) |
| rSO2 calculation formula 6 mm | | IF(H5 <= 1,100 × (1.09 − H5)/0.18, 100 × (1.08 − H5)/0.16) |
| rSO2 calculation formula 3 mm | | IF(H5 <= 1,100 × (1.065 − H5)/0.13, 100 × (1.05 − H5)/0.1) |
| rSO2 calculation formula 2.5 mm | | IF(H5 <= 1,100 × (1.065 − H5)/0.13, 100 × (1.038 − H5)/0.076) |
| rSO2 calculation formula 2 mm | | IF(H5 <= 1,100 × (1.05 − HS)/0.1, 100 × (1.015 − HS)/0.03) |

Distance to the light emitting unit 111 and that to the light receiving unit 112 are generally selected as shown in the following Table 6 based on the depth of the target tissue to be measured. Since the position where the capillary vessels situate is different depending on the depth and the portion of the target tissue to be measured, it is necessary to determine the optimal calculation formula and constants individually in order to determine accurate values.

TABLE 6

| 40 mm | Head of adult |
| 30 mm | Head of women or children, large muscle tissue |

TABLE 6-continued

| | |
|---|---|
| 20 mm | Head of newborn, small muscle tissue |
| 10 mm~2 mm | Tissue at shallow position (epideimis and dermis, brain parenchyma, intestinal tract, organ parenchyma, etc.) |

When the blood oxygen saturation in the biological body is measured by utilizing near infrared light, it is required for measurement while selecting a portion where the target tissue containing blood is present in the biological body. For example, in a case where the target tissue to be measured is a cerebral cortex of an adult, since the cerebral cortex is present at a depth of about 17 mm to 25 mm from the epidermis through the skull, about 70 to 80% for the distance between the light emitting unit 111 and the light receiving unit 112 of the probe 110 is a maximum measureable depth. Accordingly, it is necessary that the distance between the light emitting unit 111 and the light receiving unit 112 of the probe 110 is 40 mm to 30 mm.

Further, in a case of measuring the blood flow only for the epidermis, since the capillary vessels of the dermis and epidermis situate at a depth of about 1.5 mm from the skin surface, a distance of about 2.5 mm to 2.0 mm is necessary between the light emitting unit 111 and the light receiving unit 112 of the probe 110 in order to obtain information only for the epidermis.

In addition, for obtaining the blood information from other target tissue than that described above, for example, in the muscle tissue or organ per se, an adequate distance is necessary between the light emitting unit 111 and the light receiving light 112 of the probe 110 according to the depth of the target tissue from the probe 110 attached to the epidermis, and it is necessary that the light emitting unit 111 emits a light of an adequate amount in accordance with the distance between the light emitting unit 111 and the light receiving unit 112.

When the distance between the light emitting unit 111 and the light receiving unit 112 of the probe 110 is different, it is necessary to set correction coefficients obtained from calculation curves in accordance with the distance between the light emitting unit 111 and the light receiving unit 112 of the probe 110 in order to improve the accuracy also for the calculation formula of the oxygen saturation.

Upon connecting the probe 110 used for the measurement to the apparatus main body 120, it is adapted such that the calibration information stored in the ROM 117 are read by the terminal equipment 130. For example, if the distance between the light emitting unit 111 and the light receiving unit 112 of the probe 110 is 40 mm, the voltage necessary for the amount of light to be applied from the light emitting unit 111 can be set to 1.0 V in view of the calculation formula in Table 2.

As the calibration information 117D of the light emitting unit 111 and the light receiving unit 112, coefficient information are stored for calibrating such that the signal levels outputted from the light receiving amplifier 114 are identical when respective near infrared light emitting diodes emit light each at a predetermined current.

As described above, optimal calculation formulas can be set based on respective calibration information of the probe 110 stored in the ROM 117 and the result of measurement can be calculated, displayed and recorded. Further, since the terminal equipment obtains optimal information by way of the apparatus main body 120 and performs measurement in the probe 110, a reproducible oxygen saturation measuring system 100 at high accuracy can be attained by merely selecting the probe 110 optimal to the depth of the target tissue intended to be measured.

Referring to the light intensity and the signal amplification factor optimal to measurement, assuming that it is optimal for the light source at 1 and the amplification factor of 200 times, at a distance of 40 mm between the light emitting unit 111 and the light receiving unit 112, the light source at ½ and the amplification factor of 50 times at a distance of 30 mm between the light emitting unit 111 and the light receiving unit 112, the light source at ⅛ and the amplification factor of 5 times at a distance of 20 mm between the light emitting unit 111 and the light receiving unit 112, the light source at ¹⁄₁₀ and the amplification factor of 1 time at a distance of 10 mm between the light emitting unit 111 and the light receiving unit 112, the light source at ¹⁄₂₀ and the amplification factor of 1 time at the distance of 6 mm between the light emitting unit 111 and the light receiving unit 112, and the light source at ¹⁄₄₀ and the amplification factor of about 1 time at the distance of 3 mm between the light emitting unit 111 and the light receiving unit 112.

Further, according to this embodiment, the distance information between the light emitting unit 111 and the light receiving unit 112 situated corresponding to the depth of the target tissue and the voltage information for applying an amount of light according to the distance between the light emitting unit 111 and the light receiving unit 112 are stored in the ROM 117 of the probe 110. It is also possible to use a configuration of emitting a necessary amount of light from the light emitting unit 111 to a biological body by storing a distinguishing information capable of distinguishing the probe 110 corresponding to the distance between the light emitting unit 111 and the light receiving unit 112, and storing the distance information corresponding to the distinguishing information and the voltage information according to the distance in the terminal equipment 130.

In the rSO2 mode, R/IR ratio is determined based on the data on every pulse by using the moving average value from 1 to 5 sec, thereby determining R/IR ratios from the data at respective wavelengths to calculate the tissue oxygen saturation (rSO2) and hemoglobin index (HbI) in view of the correlation between the calculated R/IR ratio and the oxygen saturation and hemoglobin index (HbI).

Further, in the SpO2 mode, the moving average value is not used as in the rSO2 mode but changes of signal values are connected continuously to recognize fluctuating traces as pulse waves. Then, the number of pulses is measured by counting the cycles turning from increase to decrease or from decrease to increase for the measured values at each of the wavelengths.

For the measurement of the arterial blood oxygen saturation in the SpO2 mode (SpO2), a constant portion with no change is excluded as the information of venal blood from the calculation target and the arterial blood oxygen saturation (SpO2) is measured by using the R/IR ratio only for the portion being changed.

Figure 4:
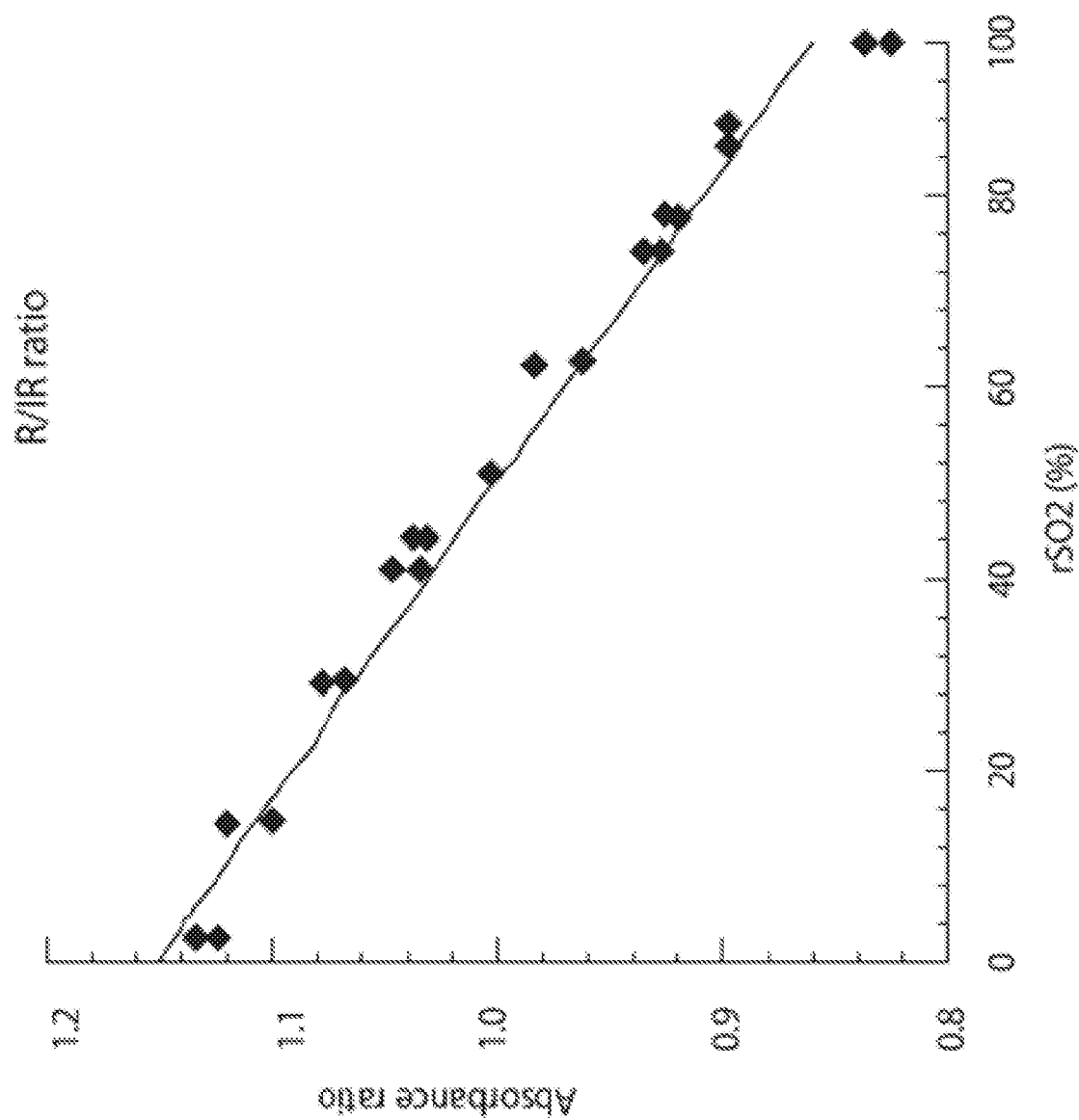
FIG. 4 is a graph showing a correlation between light absorbance ratio (R/IR ratio) and oxygen saturation.

FIG. 4 is a graph illustrating a correlation between an absorbance ratio (R/IR ratio) and oxygen saturation. FIG. 4 is a reference view of a graph showing a correlation between an absorbance ratio (R/IR ratio) and oxygen saturation of a grey vinyl chloride resin plate. The oxygen saturation is 50% when the amount of the oxyhemoglobin in which hemoglobin and oxygen are bonded is equal with the amount of deoxyhemoglobin in which oxygen is detached from oxyhemoglobin. In the present invention, it is calibrated such that the oxygen saturation is 50% when the absorbance ratio at two types of light wavelengths (R/IR ratio) is 1.0 on the phantom.

Figure 5:
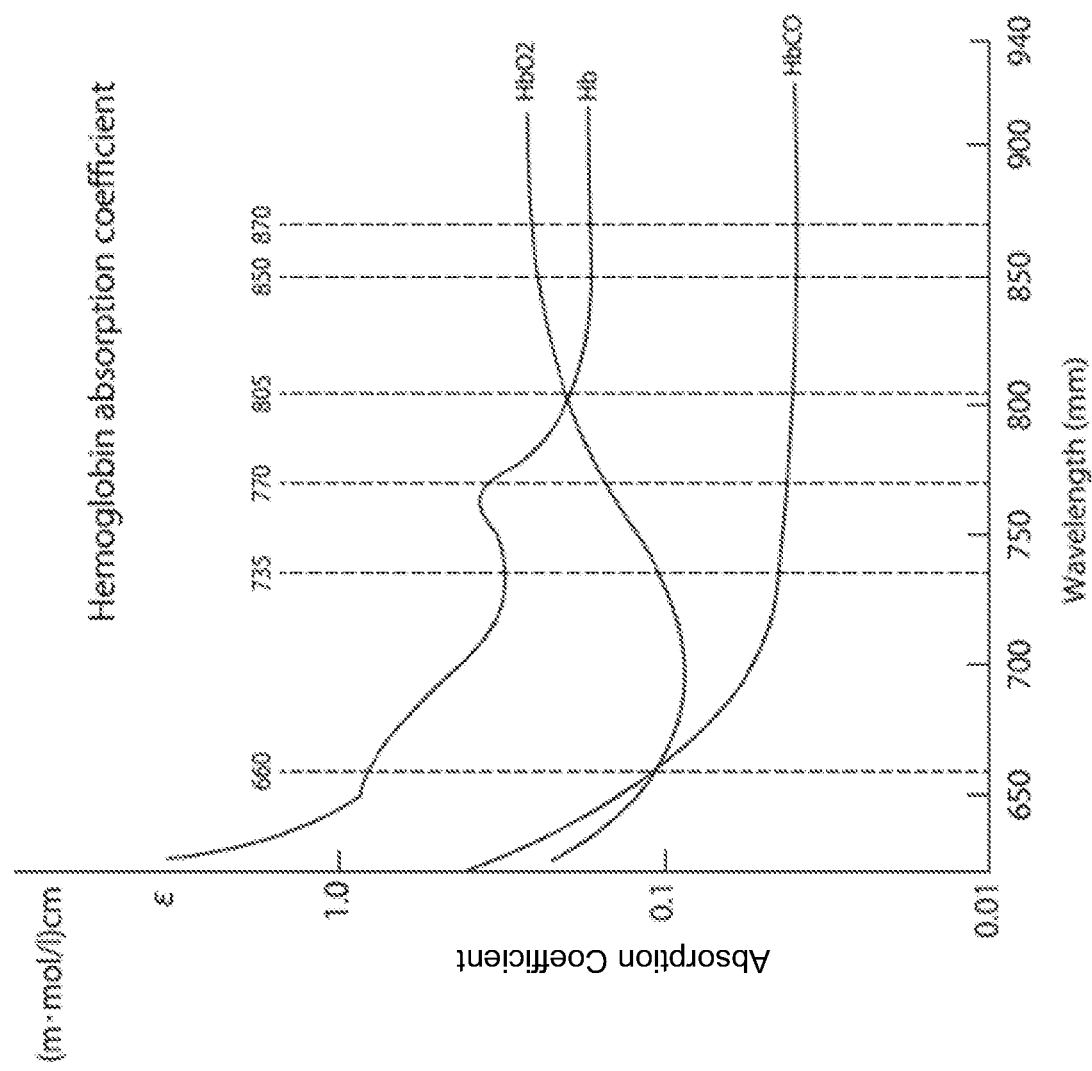
FIG. 5 is a graph showing light absorption coefficients of hemoglobins.

FIG. 5 is a graph showing the change in the absorption coefficient of oxyhemoglobin, deoxyhemoglobin, and carboxyhemoglobin. Light absorbance due to hemoglobin is different depending on the wavelength of applied light and the light at 805 nm is a wavelength showing equal absorbance which is identical between oxyhemoglobin and deoxyhemoglobin.

What is claimed is:

1. An oxygen saturation measuring apparatus for measuring oxygen saturation of a biological body by measuring near infrared light emitted from light emitting circuitry to the biological body and received by light receiving circuitry, the apparatus comprising:
    a probe including:
        an information storage device configured to store a distance information between the light emitting circuitry and the light receiving circuitry situated corresponding to a depth of a target to be measured for tissue oxygen saturation, and
        light emission driving circuitry configured to make light emit from the light emitting circuitry in an amount of light corresponding to the distance information,
    a controller connected to the probe, the controller configured to provide first control pulses to the light emission driving circuitry of the probe such that the light emitting circuitry emits light pulses configured to measure the tissue oxygen saturation, and
    the controller further configured to provide second control pulses to the light emission driving circuitry of the probe such that the light emitting circuitry emits light pulses configured to measure arterial blood oxygen saturation, wherein the controller provides the second control pulses for a predetermined time.

2. The oxygen saturation measuring apparatus according to claim 1, wherein the controller is
    configured to calculate an ambient light signal corresponding to ambient light in proximity to the light receiving circuitry, the ambient light signal is based on a difference between a first light signal measured by the light receiving circuitry resulting from light emitted by the light emitting circuitry and a second light signal measured by the light receiving circuitry resulting from an absence of light from the light emitting circuitry.

3. The oxygen saturation measuring apparatus according to claim 2, comprising
    a probe detachment warning device configured to judge detachment of the light receiving circuitry from the biological body and output a warning when the second light signal measured by the light receiving circuitry exceeds a predetermined level.

4. The oxygen saturation measuring apparatus according to claim 1, wherein the controller is configured to determine a tissue oxygen saturation level and
    to provide the second control pulses to the probe upon the tissue oxygen saturation level being below a predetermined threshold.

5. The oxygen saturation measuring apparatus according to claim 4, comprising
    a pulseless state warning outputting device configured to output a warning when pulsation cannot be detected from measured arterial blood oxygen saturation when providing the second control pulses to the probe upon the tissue oxygen saturation level being below the predetermined threshold.

6. The oxygen saturation measuring apparatus according to claim 1, wherein the controller is
    configured to periodically provide the second control pulses to the probe.

7. The oxygen saturation measuring apparatus according to claim 1, wherein the probe comprises:
    a light receiving amplifier configured to amplify an analog signal of a light received by the light receiving circuitry, and
    an analog/digital converter coupled to the light receiving amplifier and configured to convert analog signals amplified by the light receiving amplifier into digital signals.

8. The oxygen saturation measuring apparatus according to claim 1, comprising a main body coupled to the probe to receive the digital signals from the analog/digital converter and wherein the main body includes
    a wireless communication device configured to wirelessly send the digital signals converted by the analog/digital converter to the controller.

9. The oxygen saturation measuring apparatus according to claim 1, wherein
    the information storage device stores f reference values with respect to transmission light measured previously by using a phantom configured to obtain absorption characteristics identical with those of the biological body and the controller is configured to execute a calculation in comparison with the reference values.

10. The oxygen saturation measuring apparatus according to claim 1, wherein
    the information storage device stores a reference value with respect to the transmitted light measured previously by using a blood adjusted to a preselected oxygen saturation and the controller is configured to execute a calculation in comparison with the reference value.

11. A probe adapted to be used in an oxygen saturation measuring apparatus configured to measure near infrared lights applied from light emitting circuitry to a biological body and received by light receiving circuitry, the probe comprising:
    an information storage device configured to store a distance information between the light emitting circuitry and the light receiving circuitry situated corresponding to the depth of an object to be measured for the tissue oxygen saturation,
    light emission driving circuitry configured to make light emit from the light emitting circuitry in an amount of light corresponding to the depth of an object, and
    a microprocessor coupled to the light emission driving circuitry, the microprocessor configured to output a control pulse to the light emission driving circuitry such that the light emitting circuitry emits light pulses configured to measure the tissue oxygen saturation.

12. The oxygen saturation measuring apparatus according to claim 1, wherein the probe is a first probe associated with a first depth of the target to be measured and the first probe is exchangeable with a second
    probe associated with a second depth of the target to be measured.

13. A method of measuring oxygen saturation of a biological body by measuring near infrared light emitted from light emitting circuitry to a biological body by light receiving circuitry, the method including:
- storing a distance information between the light emitting circuitry and the light receiving circuitry situated corresponding to a depth of a target to be measured for the tissue oxygen saturation by an information storage device,
- making the light emitting circuitry emit a light in an amount corresponding to the distance information by light emission driving circuitry,
- providing first control pulses to the light emitting circuitry such that the light emitting circuitry emits light pulses configured to measure tissue oxidation saturation, and
- providing second control pulses to the light emitting circuitry for a predetermined time such that the light emitting circuitry emits light pulses configured to measure an arterial oxygen saturation.

14. The probe according to claim 11, wherein the microprocessor is further configured to provide second control pulses to the light emission driving circuitry such that the light emitting circuitry emits light pulses configured to measure arterial blood oxygen saturation, wherein the microprocessor provides the second control pulses for a predetermined time period.

15. The probe according to claim 14, wherein the microprocessor is configured to provide the first control pulses to the light emission driving circuitry upon the expiration of the predetermined time period.

16. The oxygen saturation measuring apparatus according to claim 1, wherein the first control pulses result in the light emitting circuitry emitting 10 light pulses per second and the second control pulses result in the light emitting circuitry emitting 30 light pulses per second.

17. The oxygen saturation measuring apparatus according to claim 1, wherein the light receiving circuitry obtains one sample per light pulse from the light emitting circuitry and holds the obtained sample until the next light pulse is provided by the light emitting circuitry.

* * * * *